United States Patent
Donahue

(10) Patent No.: US 12,117,114 B2
(45) Date of Patent: Oct. 15, 2024

(54) CLEANROOM WALL PASSTHROUGH

(71) Applicant: Fast Valve LLC, Kirkland, WA (US)

(72) Inventor: John Donahue, Kirkland, WA (US)

(73) Assignee: Fast Valve LLC, Kirkland, WA (US)

( * ) Notice: Subject to any disclaimer, the term of this patent is extended or adjusted under 35 U.S.C. 154(b) by 166 days.

(21) Appl. No.: 17/470,954

(22) Filed: Sep. 9, 2021

(65) Prior Publication Data

US 2023/0075726 A1 Mar. 9, 2023

(51) Int. Cl.
*F16L 5/10* (2006.01)
*F16K 27/02* (2006.01)

(52) U.S. Cl.
CPC ............ *F16L 5/10* (2013.01); *F16K 27/0236* (2013.01)

(58) Field of Classification Search
CPC ....... F16L 5/10; F16L 5/02; F16L 5/14; F16L 41/088; F16L 41/12; C12M 37/00; H02G 3/32
USPC .................................................. 285/194, 215
See application file for complete search history.

(56) References Cited

U.S. PATENT DOCUMENTS

| | | | | |
|---|---|---|---|---|
| 4,619,545 A | * | 10/1986 | Kuttenbaum | F16B 7/04 403/373 |
| 4,702,444 A | * | 10/1987 | Beele | H02G 3/22 174/151 |
| 4,889,298 A | | 12/1989 | Hauff | |
| 4,919,372 A | * | 4/1990 | Twist | H02G 3/22 248/68.1 |
| 5,108,060 A | * | 4/1992 | Beele | F16L 5/14 52/220.8 |
| 6,390,135 B1 | | 5/2002 | Shimizu | |
| 6,668,864 B2 | | 12/2003 | Shimizu | |
| 7,005,579 B2 | | 2/2006 | Beele | |
| 7,355,130 B2 | * | 4/2008 | Holman | H02G 3/088 174/152 G |
| 8,541,699 B2 | * | 9/2013 | Milton | F16L 5/08 174/152 G |
| 8,870,230 B2 | | 10/2014 | Bibbo | |
| 9,263,872 B2 | | 2/2016 | Sims et al. | |
| 9,869,408 B2 | | 1/2018 | Bibbo | |
| 9,920,859 B2 | | 3/2018 | Perrigo et al. | |
| 10,113,670 B2 | | 10/2018 | Bibbo et al. | |
| 10,461,463 B2 | * | 10/2019 | Schoenfeld | H01R 13/518 |
| 10,488,074 B2 | | 11/2019 | Yoskowitz | |
| 2013/0307225 A1 | * | 11/2013 | Boyd | H02G 3/185 277/626 |
| 2021/0328416 A1 | * | 10/2021 | Ehmann | F16L 5/10 |

* cited by examiner

*Primary Examiner* — James M Hewitt, II
(74) *Attorney, Agent, or Firm* — CHRISTENSEN O'CONNOR JOHNSON KINDNESS PLLC

(57) ABSTRACT

A passthrough for a barrier separating a first space from a second space includes a housing mounted to an opening that extends through the barrier. First and second doors selectively block the first and second spaces, respectively, from the opening. A frame is disposed within the housing and has first and second apertures configured to receive sealing blocks. When the passthrough is in a first state, sealing blocks seal the first and second apertures. When the passthrough is in a second state, a fluid conduit passes through the first and second apertures and sealing blocks seal the space between the first and second apertures, respectively, and the conduit.

17 Claims, 14 Drawing Sheets

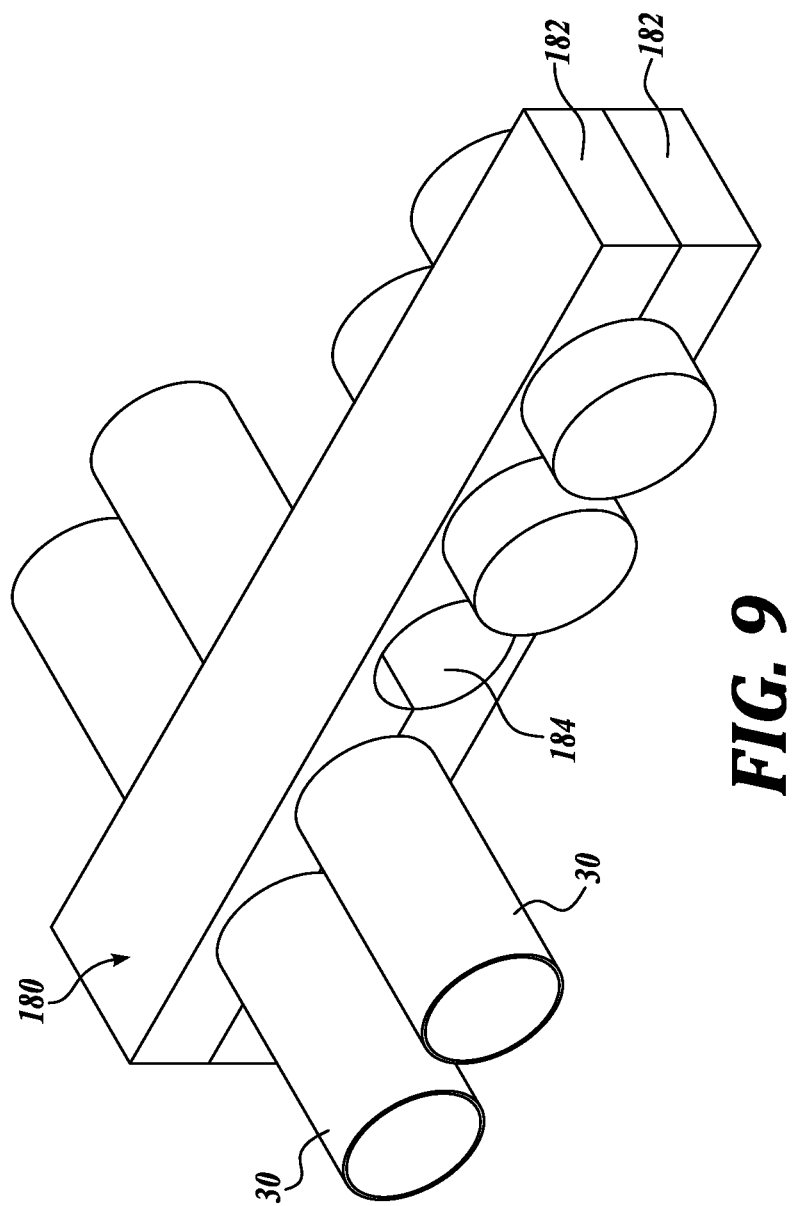

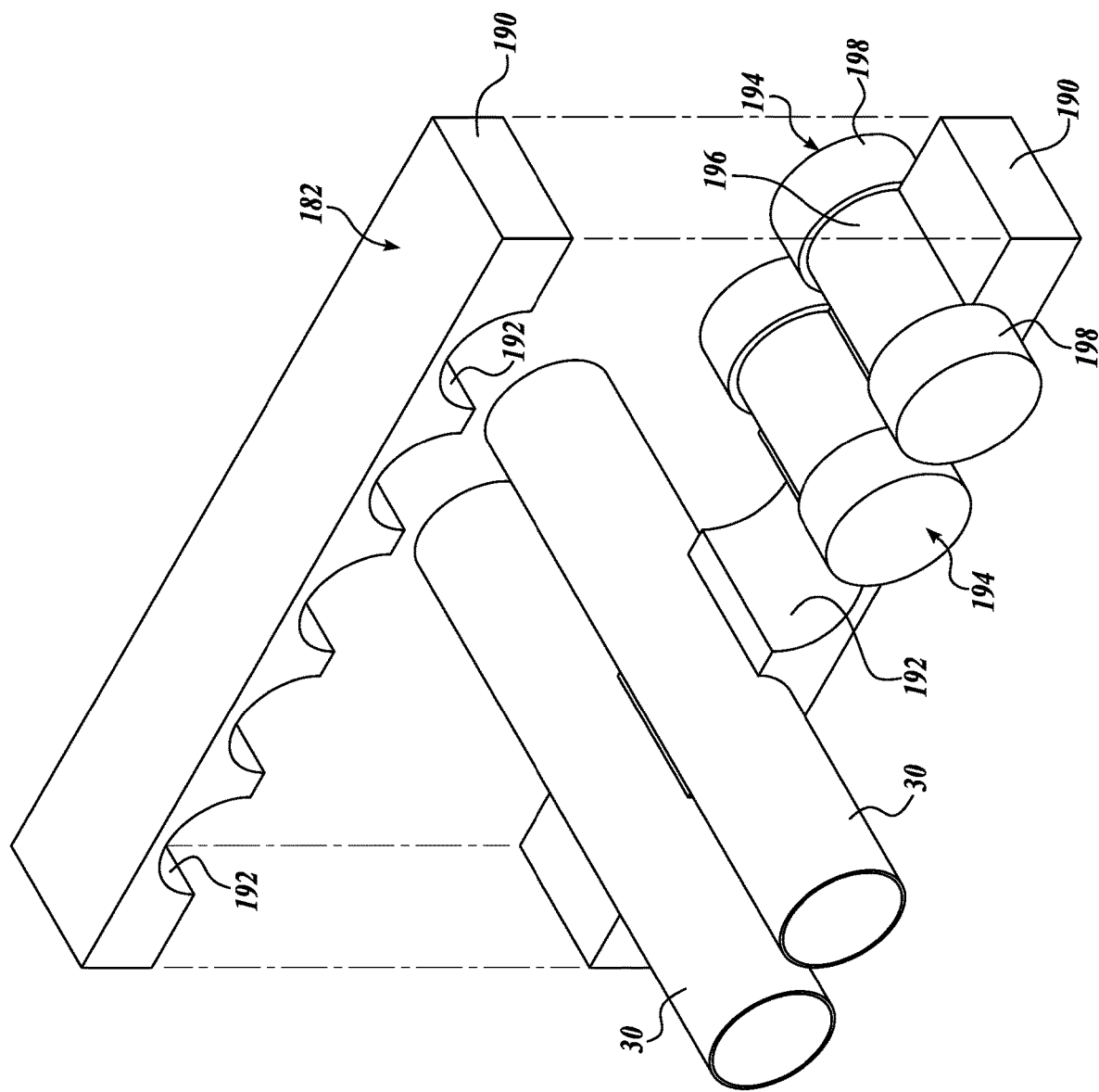

CLEANROOM WALL PASSTHROUGH

BACKGROUND

Cleanrooms provide controlled environments for the manufacturing and processing of pharmaceutical products, medical equipment, electronic products, and other products that require a pollutant-free environment. In order to transfer materials from "dirty" environments into cleanrooms, wall passthroughs are used to maintain the integrity of the cleanroom. To move fluids into cleanrooms, conduits, such as hoses or tubing extend through an opening in the wall, and the exterior surface of the conduit is sealed against the wall on each side of the wall to prevent contaminates from entering the cleanroom through the opening around the conduit. These configurations also prevent potentially hazardous materials from exiting the cleanroom.

Known passthroughs that accommodate transfer of fluids are cumbersome and not easily switched between a first state, in which the entire opening is sealed, and a second state, in which a conduit provides a fluid passageway through an otherwise sealed opening.

SUMMARY

Disclosed embodiments of a passthrough are described to selectively isolate a first and second spaces, while allowing of the transfer of fluid and other materials between the spaces. In a representative embodiment, a passthrough includes a barrier that separates a first space from a second space, the barrier having a first side at least partially defining a portion of the first space and a second side at least partially defining a portion of the second space. The barrier further includes an opening extending from the first space to the second space. The passthrough has a housing mounted to the barrier and extending through the opening so that the housing defines a passageway that extends from the first side of the barrier to the second side of the barrier. The housing also includes a first door that selectively separates at least a portion of the opening from the first space and a second door that selectively separates at least a portion of the opening from the second space.

A frame is disposed within the housing and has a first recess proximate to the first space and a second recess proximate to the second space. The first and second recesses are configured to receive first and second sealing blocks, respectively, each of which includes an aperture extending therethrough. The passthrough is selectively configurable to have a first state and a second state. In the first state, the first and second sealing blocks seal the first and second recesses, respectively. In the second state, a first fluid conduit passes through the first and second recesses, and the first and second sealing blocks seal a space between the first and second recesses, respectively, and the first conduit.

In some embodiments, the first conduit extends through the aperture in each of the first and second sealing blocks when the passthrough is in the second state.

In some embodiments, the first and second doors and the first and second sealing blocks cooperate to isolate the first space from the second space when the passthrough is in the first state.

In some embodiments, the first and second doors and the first and second sealing blocks cooperate to isolate the portion of the passthrough surrounding the first conduit from the first and second spaces when the passthrough is in the second state.

In some embodiments, the aperture of the first sealing block is fluidly isolated from the first space when the passthrough is in the first state.

In some embodiments, the aperture of the second sealing block is fluidly isolated from the second space when the passthrough is in the first state.

In some embodiments, the first block is selectively positionable relative to the frame to transition the passthrough between the first and second states.

In some embodiments, the first sealing block is rotatable to occlude the first recess when the passthrough is in the first state.

In some embodiments, the first sealing block comprises a first portion engaging a second portion to define the aperture.

In some embodiments, the first portion is identical to the second portion.

In some embodiments, the first sealing block includes a first portion slidably associated with a second portion, the first portion being selectively movable relative to the second portion so that the first sealing block occludes the first recess when the passthrough is in the first state and the first and second portions define the aperture when the passthrough is in the second state.

In some embodiments, the first portion is selectively positionable relative to the second portion to define apertures of different sizes.

In some embodiments, the passthrough further includes a plug selectively insertable into the aperture of the first sealing block, wherein the plug occludes the aperture of the first sealing block when inserted in the aperture.

In some embodiments, the passthrough further includes a valve disposed within the housing, wherein the valve selectively controls a flow of fluid through the first conduit.

In some embodiments, the passthrough further includes a second conduit extending into the housing and a manifold disposed within the housing, the manifold fluidly connecting the first and second conduits.

In some embodiments, the passthrough further includes a panel supported by the frame and separating the passageway into a first portion and a second portion.

In another representative embodiment, a passthrough is suitable for use with a barrier that separates a first space from a second space, the barrier having a first side at least partially defining a portion of the first space and a second side at least partially defining a portion of the second space. The barrier further includes an opening extending from the first space to the second space. The passthrough has a housing mounted to the barrier and extending through the opening so that the housing defines a passageway that extends from the first side of the barrier to the second side of the barrier. A first door selectively separates at least a portion of the opening from the first space, and a first valve is mounted to the first door. The passthrough is selectively configurable to have a first state and a second state, wherein the first valve and the first door isolate the passageway from the first space when the passthrough is in the first state, and the first valve sealingly engages a fluid conduit passing therethrough when the passthrough is in the second state.

In some embodiments, the passthrough further includes a second door selectively separating at least a portion of the opening from the second space, and a second valve mounted to the second door. The second valve and the second door isolate the passageway from the second space when the passthrough is in the first state, and the second valve sealingly engages the fluid conduit passing therethrough when the passthrough is in the second state.

In some embodiments, the first and second valves are iris valves.

In some embodiments, the first valve comprises a diaphragm defining an aperture with a variable diameter.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of the present disclosure will become more readily appreciated as the same become better understood by reference to the following detailed description, when taken in conjunction with the accompanying drawings, wherein:

FIG. 9 an isometric view of a second representative embodiment of a sealing block suitable for use with the passthrough of FIG. 1;

FIG. 10 shows an isometric exploded view thereof;

DETAILED DESCRIPTION

The detailed description set forth below in connection with the appended drawings, where like numerals reference like elements, are intended as a description of various embodiments of the present disclosure and are not intended to represent the only embodiments. Each embodiment described in this disclosure is provided merely as an example or illustration and should not be construed as precluding other embodiments. The illustrative examples provided herein are not intended to be exhaustive or to limit the disclosure to the precise forms disclosed.

In the following description, specific details are set forth to provide a thorough understanding of exemplary embodiments of the present disclosure. It will be apparent to one skilled in the art, however, that the embodiments disclosed herein may be practiced without embodying all of the specific details. In some instances, well-known process steps have not been described in detail in order not to unnecessarily obscure various aspects of the present disclosure. Further, it will be appreciated that embodiments of the present disclosure may employ any combination of features described herein.

The present application may include references to directions, such as "forward," "rearward," "front," "rear," "upward," "downward," "top," "bottom," "right hand," "left hand," "lateral," "medial," "in," "out," "extended," etc. These references, and other similar references in the present application, are only to assist in helping describe and to understand the particular embodiment and are not intended to limit the present disclosure to these directions or locations.

The present application may also reference quantities and numbers. Unless specifically stated, such quantities and numbers are not to be considered restrictive, but exemplary of the possible quantities or numbers associated with the present application. In this regard, the present application may use the term "plurality" to reference a quantity or number. In this regard, the term "plurality" is meant to any number that is more than one, for example, two, three, four, five, etc. The terms "about," "approximately," "near," etc., mean plus or minus 5% of the stated value. For the purposes of the present disclosure, lists of two or more elements of the form, for example, "at least one of A, B, and C," is intended to mean (A), (B), (C), (A and B), (A and C), (B and C), or (A, B, and C), and further includes all similar permutations when any other quantity of elements is listed.

The following description provides several examples that relate to a passthrough for selectively isolating a cleanroom from an exterior area. Embodiments of the passthrough provide for the use of conduits to pass large volumes of fluids into and out of the cleanroom without putting the clean room in fluid connection with the exterior area.

Figure 1:
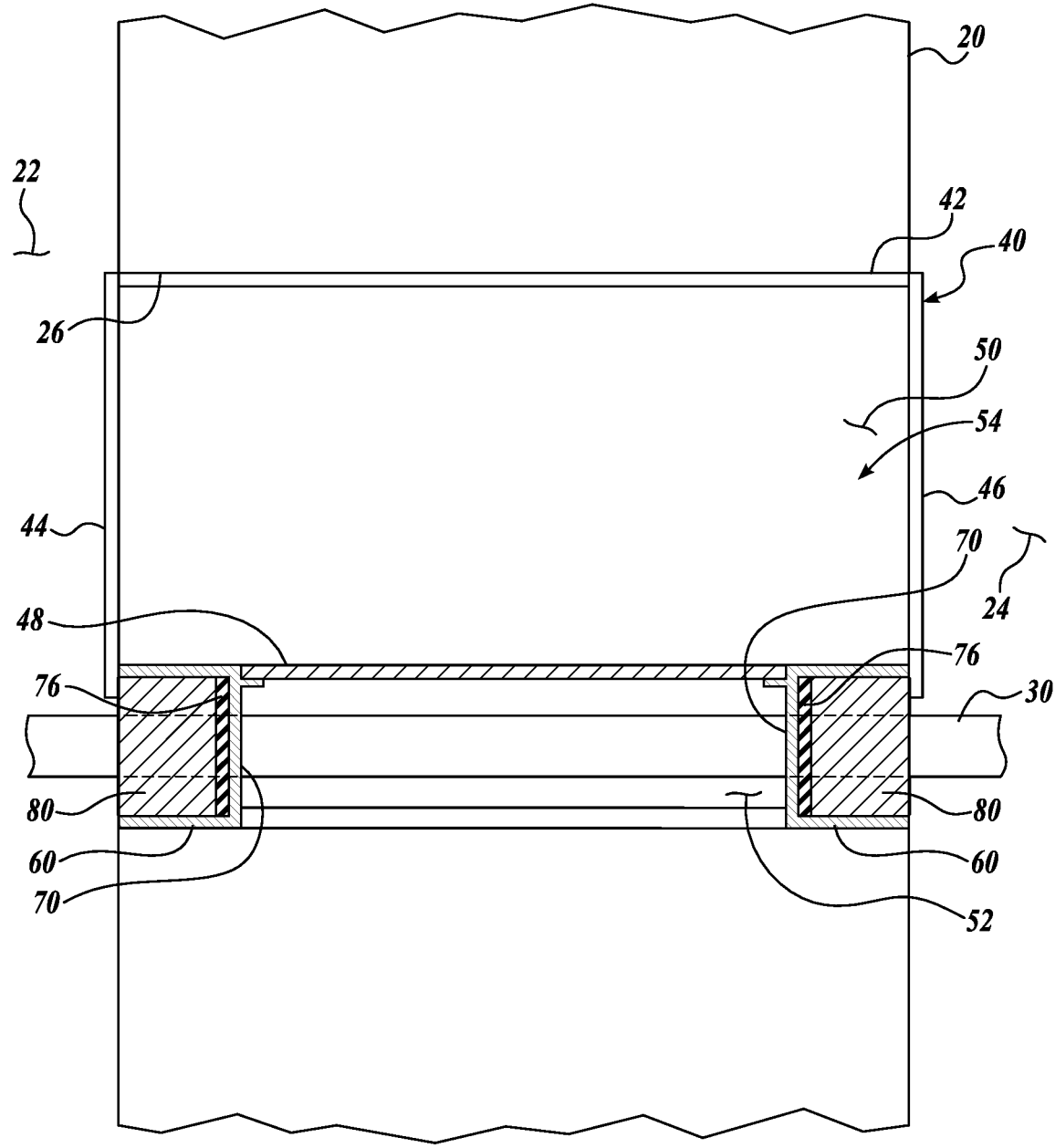
FIG. 1 shows a cross-sectional view of a first representative embodiment of a passthrough according to aspects of the present disclosure, wherein the passthrough is mounted in a wall.
Figure 2:
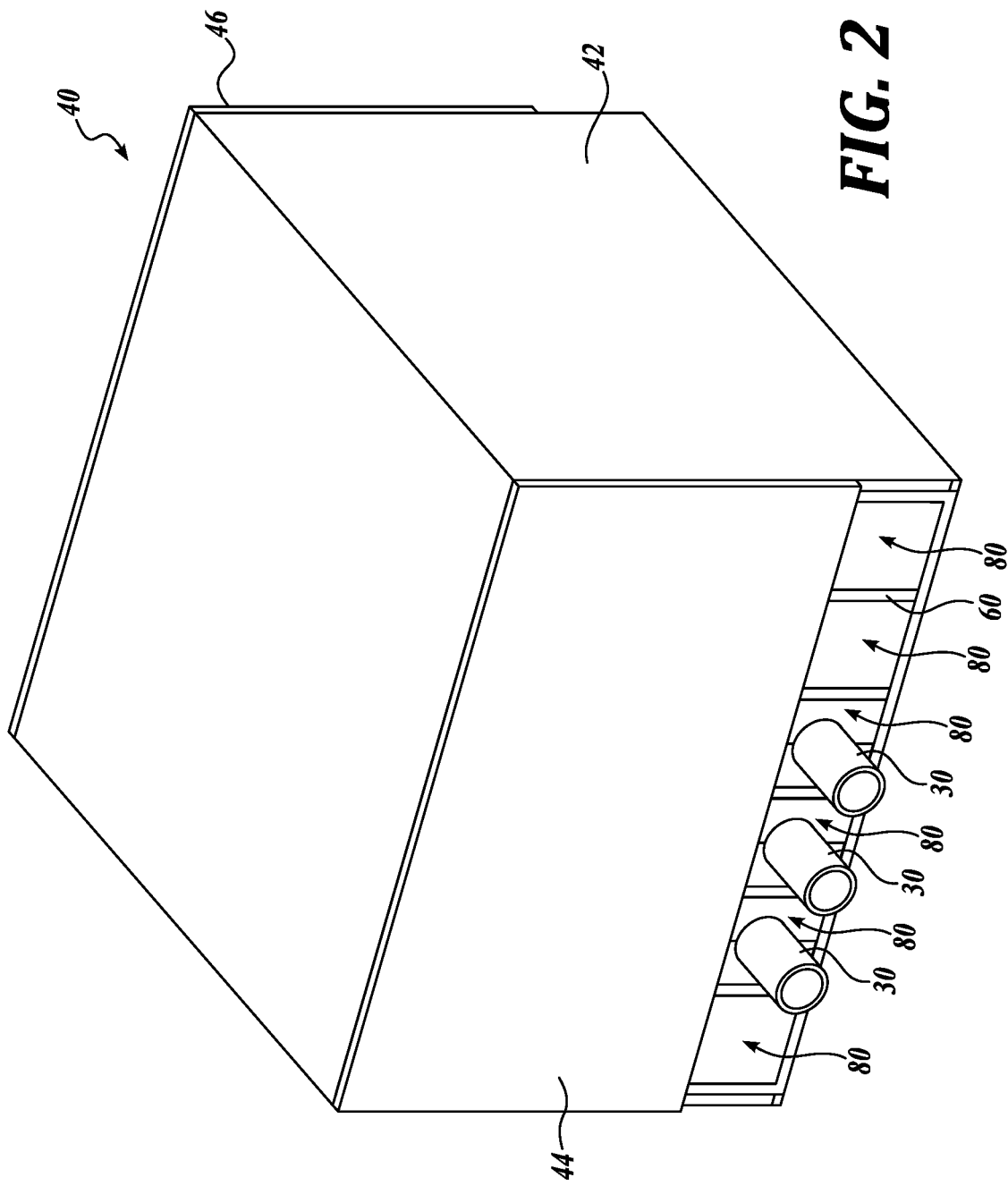
FIG. 2 shows an isometric view of the passthrough of FIG. 1, wherein first and second doors are in a closed position.
Figure 3:
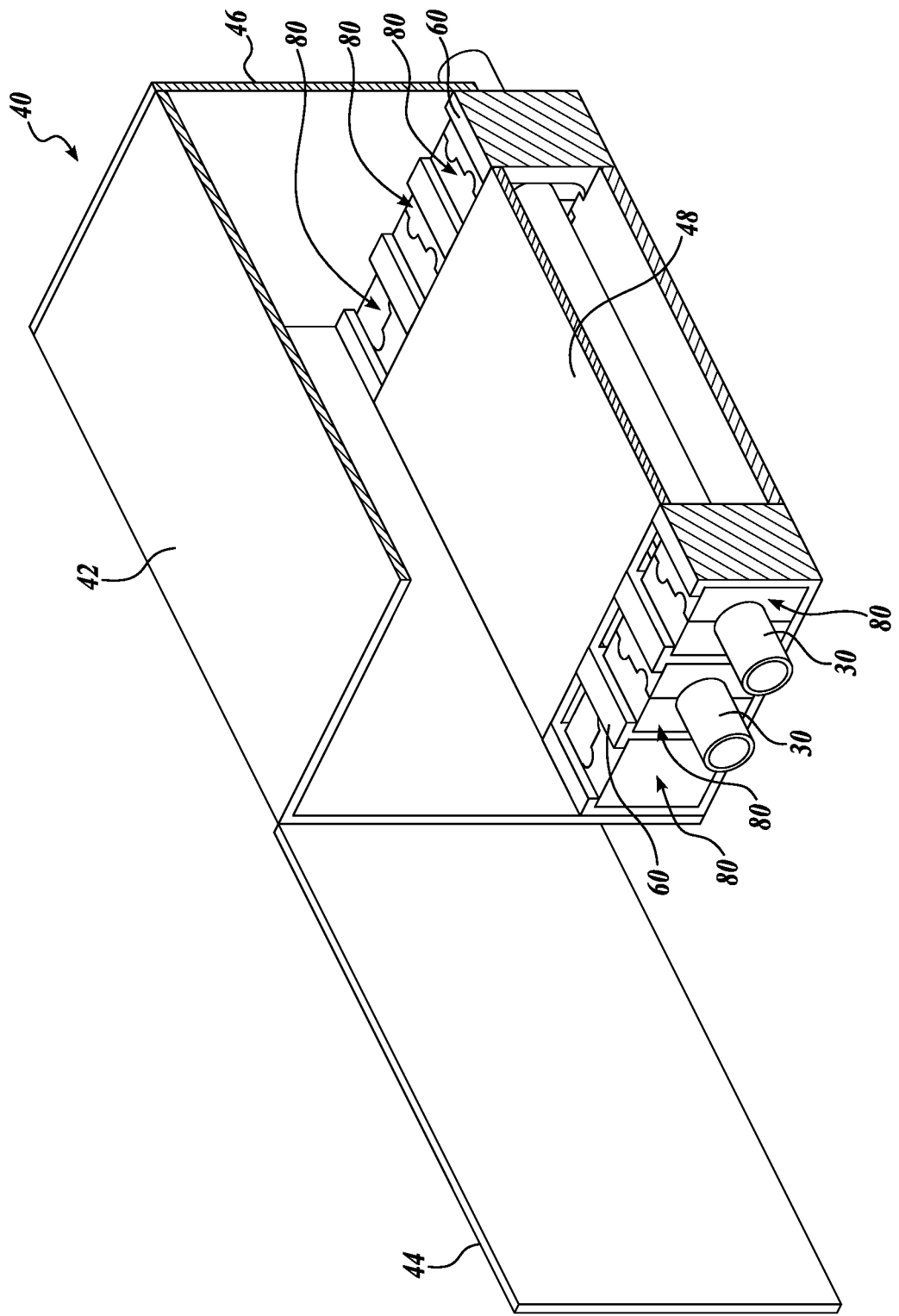
FIG. 3 shows a partial isometric view of the passthrough of FIG. 1, wherein the first door is in an open position.

Referring initially to FIGS. 1-3, a first representative embodiment of a passthrough 40 according to the present disclosure is shown. The illustrated passthrough 40 is mounted in an opening 26 that extends through a barrier 20 from a first area 22 to a second area 24. In some embodiments, the barrier 20 is a wall that separates a cleanroom (first area 22) from an area (second area 24) external to the cleanroom. In some embodiments, the barrier 20 is a window, a door, or any other structure or combination of structures that separate a first area from a second area. In some embodiments, the barrier 20 separates a cleanroom from two or more areas external to the cleanroom, including other cleanrooms. In some embodiments, the barrier forms a corner of a cleanroom.

The passthrough 40 includes a generally box-shaped housing 42 with an outer profile corresponding to the surface of the opening 26. A frame 60 is positioned at each end of the housing 42, and each frame is configured to receive one or more sealing blocks 80. A removable panel 48 is supported by the frames 60 and cooperates with the frames and the sealing blocks 80 to separate the housing into a first (upper) portion 50 and a second (lower) portion 52 that collectively form a passageway 54 through the housing.

Figure 4:
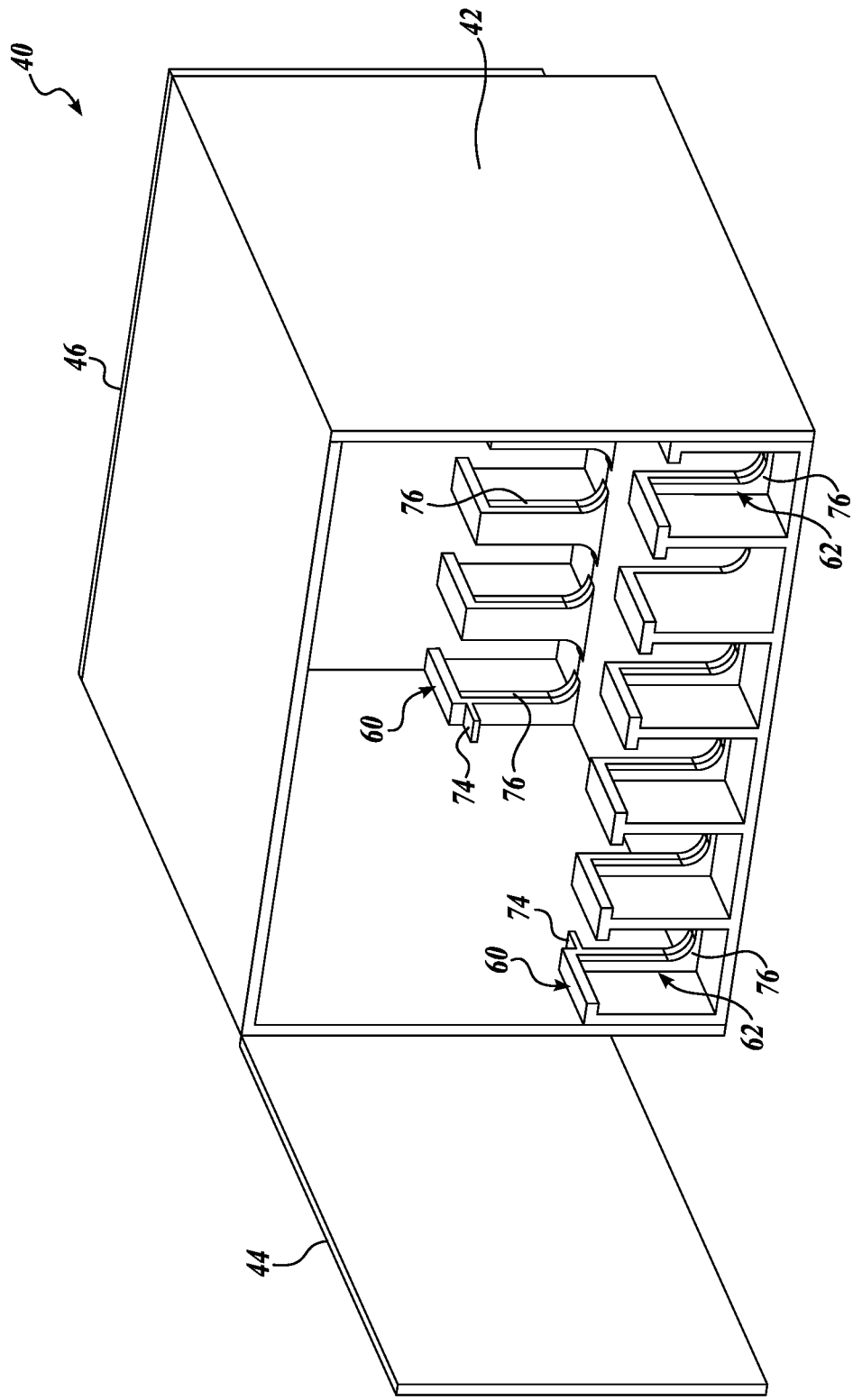
FIG. 4 shows a partial isometric view of a housing of the passthrough of FIG. 1.

As shown in FIG. 4, in the illustrated embodiment, a plurality of frame supports 74 are formed on the frame 60 to support the panel 48, however, it will be appreciated that any suitable configuration to support the panel may be included. In some embodiments, the passthrough 40 can be operated with the panel removed. In some embodiments, the passthrough 40 does not have a panel. As will be described in further detail, the first portion 50 like known passthroughs that allow materials to be moved from a "dirty" area to a cleanroom without contaminating the cleanroom. The second portion 52 provides an area through which conduits may be selectively installed to move fluids to the cleanroom.

Still referring to FIGS. 1-3, a first door 44 is hingedly coupled to the housing 42 proximate to the first area 22. The first door 44 is selectively moveable between a closed position, as shown in FIG. 1, and an open position, shown in FIG. 3. When the first door 44 is in the open position, access is provided to the first portion 50 of the passthrough 40 from the first area 22. When the first door 44 is in the closed position, the door isolates the first portion 50 of the passthrough 40 from the first area 22.

A second door 46 is hingedly coupled to the housing 42 proximate to the second area 24. Similar to the first door 44, the second door 46 is selectively moveable between an open position and a closed position, wherein when the second door 46 is in the open position, access is provided to the first portion 50 of the passthrough 40 from the second area 24, and when the second door 46 is in the closed position, the door isolates the first portion of the passthrough 40 from the second area 24. In some embodiments, an interlock (not shown) is provided to prevent one of the doors 44, 46 from being moved toward the open position unless the other door is in the closed position. In this regard, the interlock ensures that the first area 22 and second area 24 are never in direct fluid connection through the first portion 50 of the passthrough 40.

The second portion 52 of the passthrough 40 provides an area through which one or more conduits 30, such as tubing, pipes, etc., can be mounted to extend between the first area 22 and the second area 24. The conduits 30 enable large amounts of liquids and/or gases to be transferred between the first area 22 and second area 24 while maintaining fluid separation between the first and second areas around the conduits.

Figure 5:
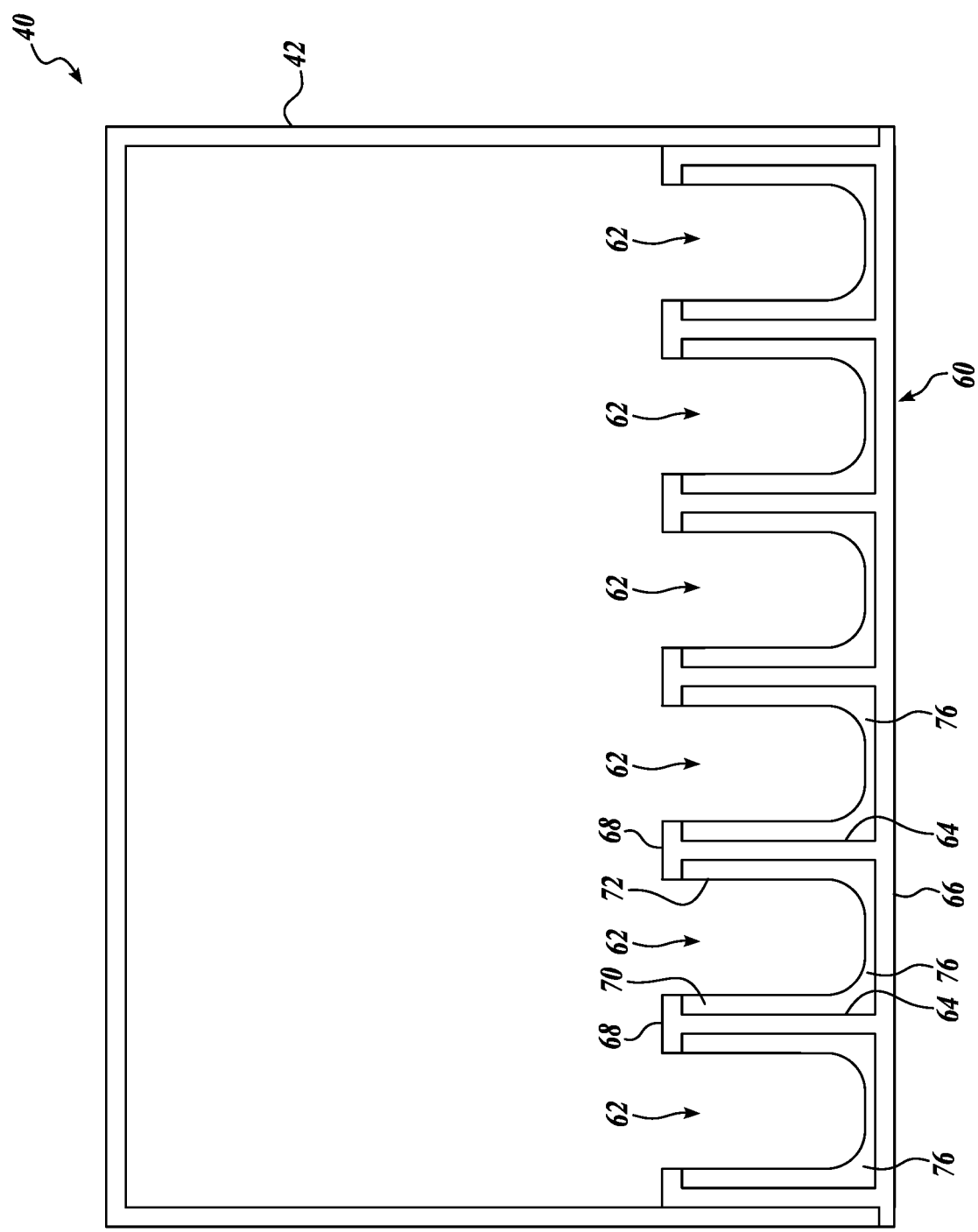
FIG. 5 shows and end view thereof.

As best shown in FIGS. 4 and 5, a frame 60 extends along the bottom edge of the housing 42 proximate to the each of the first area 22 and the second area 24. Each frame includes a plurality of vertical walls 64 extending upward from a base 66. Each vertical wall 64 includes a cap 68 extending laterally from the top of the vertical wall. The frame further includes an inner wall 70 that is offset from the opening of the housing 42 and extends upward from the base 66 to be generally perpendicular to the vertical walls 64. The base 66, adjacent vertical walls 64, the corresponding caps 68, and the inner wall 70 cooperate to define a recess 62 sized to slidable receive a sealing block 80 therein. The inner wall 70 includes a U-shaped cutout 72 between each pair of adjacent vertical walls 64. Each cutout 72 is sized to allow a conduit 30 to extend through the recess 62 in a horizontal direction. In some embodiments, two or more frames are used. In some embodiments, a single frame is configured to extend across the passthrough 40 and have recesses 62 formed proximate to both ends of the passthrough.

Figure 6:
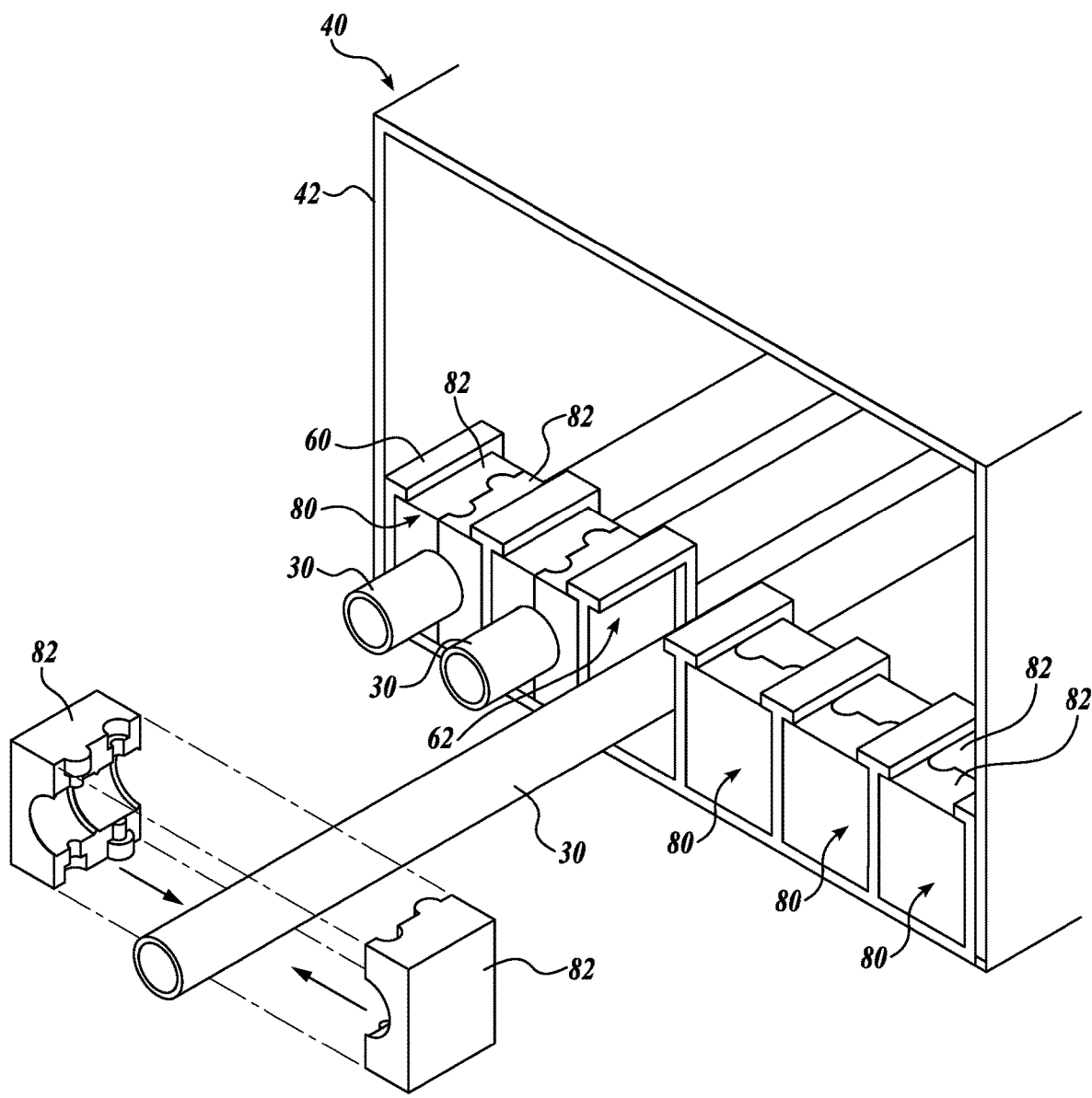
FIG. 6 shows a partially exploded view of a sealing block of the passthrough of FIG. 1.

Referring now to FIG. 6, to mount a conduit 30 to the passthrough 40, the conduit is positioned to extend through one of the recess 62 in one of the frames 60. In the illustrated embodiment, the cutout 72 in the inner wall 70 of the frame 60 enables a user to lower a portion of the conduit 30 into the recess 62 from above. A sealing block 80 is mounted to the conduit 30 to sealingly engage the outer perimeter of the conduit. The sealing block 80 is then inserted into the recess 62. When inserted in the recess 62, the sides of the sealing block sealingly engage the base 66, vertical walls 64, and, optionally, the caps 68 and inner wall 70.

As best shown in FIGS. 1 and 2, when the door 44, 46 is closed, the sealing block 80 sealingly engages the door across the top of the sealing block. Thus, the door 44, 46, and the vertical walls 64 and base 66 of the recess 62 are in sealing engagement with the outer perimeter of the sealing block, and the sealing block is also in sealing engagement with the outer perimeter of the conduit, so that the interior portion of the passthrough 40 is sealed.

Referring back to FIG. 6, the illustrated frame 60 includes a plurality of recesses 62 that allow for different numbers of conduits 30 to be mounted to the passthrough 40 as needed. For those recesses 62 through which a conduit 30 is secured, a sealing block 80 secures the conduit with the aperture and also occludes the aperture around the conduit. For those recesses 62 through which a conduit 30 is not secured, a sealing block 80 occludes the entire aperture. That is, a sealing block 80 is mounted within the aperture and sealingly engages the door 44, 46 (when closed) and the vertical walls 64 and 66 of the recess 62 to isolate the first portion 50 of the passthrough 40 from the adjacent external area 22, 24.

In some embodiments, the passthrough 20 includes a gasket 76 disposed between the inner wall 70 and the sealing block 80 to at least partially seal the area between the recess 62 and the sealing block 80. In some embodiments, an O-ring extends around the sealing block 80 to at least partially seal the area between the recess 62 and the sealing block 80. These and other suitable sealing configurations or combinations of sealing configurations can be included to reduce or eliminate air flow between the sealing block(s) 80 and the recess(es) 62, and such embodiments should be considered within the scope of the present disclosure. In this regard, some leaking may be acceptable, particularly active ventilation or dynamic passthroughs.

Figure 8:
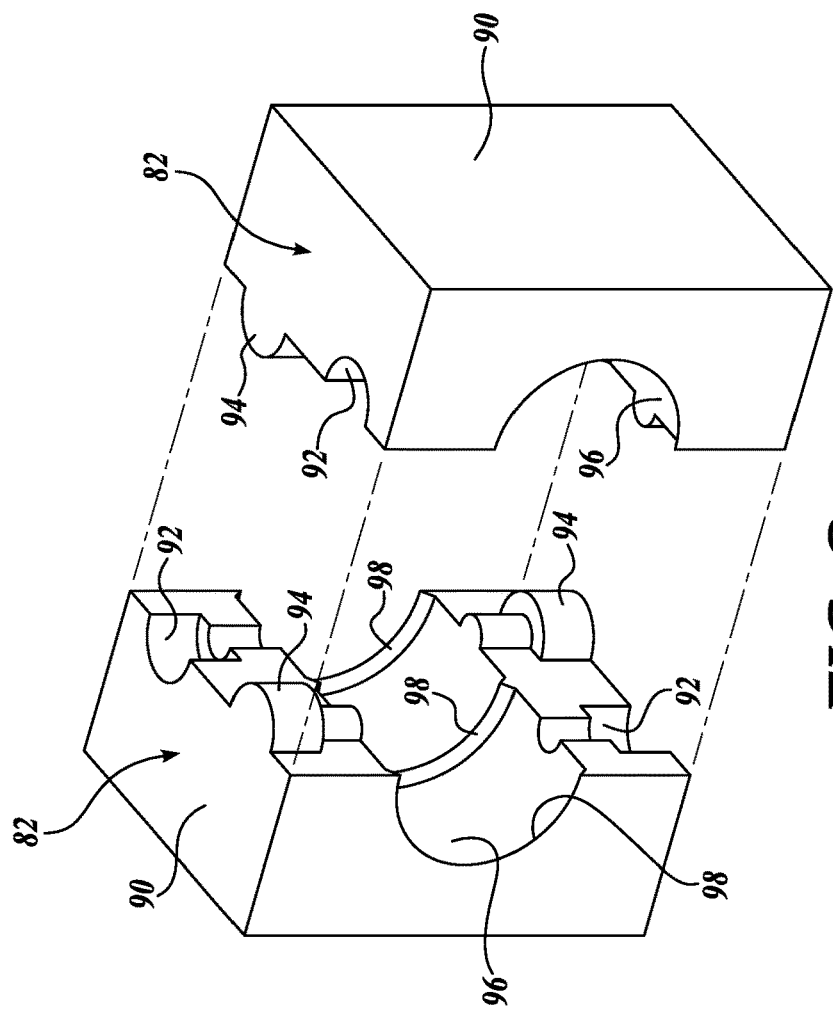
FIG. 8 shows an isometric exploded view thereof.
Figure 7:
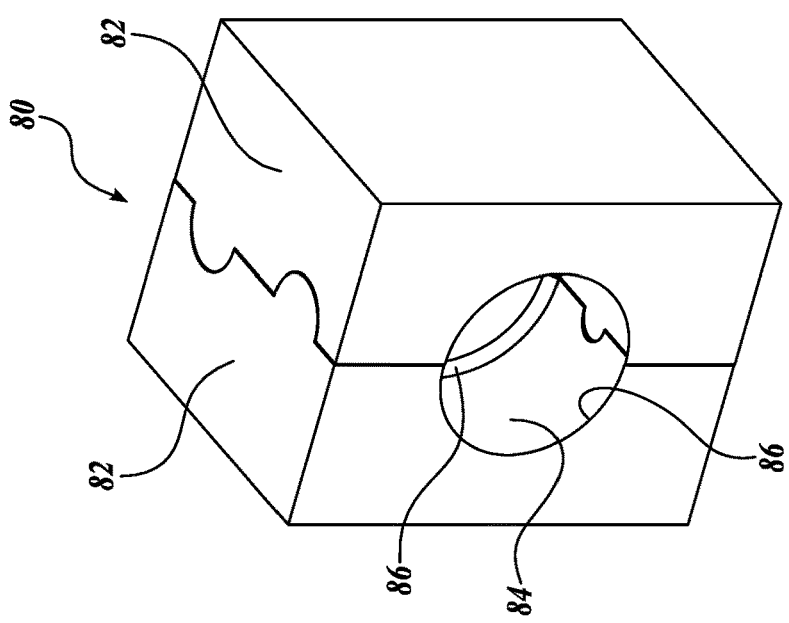
FIG. 7 shows an isometric view of the sealing block of FIG. 6.

FIGS. 7 and 8 show a first representative embodiment of a sealing block 80 suitable for use with the embodiments of the passthrough 40 according to the present disclosure. The sealing block 80 is formed from two seal portions 82. Each seal portion 82 is preferably made from a material that can be cleaned/sterilized, such as with an autoclave. In one nonlimiting example, the sealing blocks 80 are made from Teflon. In some embodiments, the sealing blocks 80 are made from a rigid material, such as a hard plastic. In some embodiments, the sealing blocks 80 are elastic and at least partially deform when inserted into the recesses 62.

In the illustrated embodiment, the two seal potions 82 are configured to be joined to form a sealing block 80 having the shape of rectangular cuboid, i.e., a hexahedron with six rectangular faces, with an aperture 84 extending therethrough to accommodate a conduit 30. A plurality of retainers 86 protrude radially inward from the surface of the aperture 84. When the sealing block 80 is mounted to a conduit 30, the retainers 86 engage the conduit to prevent or limit movement of the conduit relative to the seal. Retention features 98 formed in each seal portion cooperate to define each retainer 86.

Each seal portion 82 includes a body 90 with one or more first locking features 92 and second locking features 94. When two seal portions 82 are assembled to form a sealing block 80 the first locking features 92 of one seal portion 82 engage the second locking features 94 of the other seal portion 82 to limit movement of the seal portions relative to each other. In the illustrated embodiment, each first locking feature 92 is a recess with coaxial semi-cylindrical portions having different diameters. Each second locking feature 94 is a protrusion with coaxial semi-cylindrical protrusions sized and configured to nest within the corresponding portions of the first locking feature 92. When engaged, the illustrated first and second locking features 92, 94 prevent movement of the seal portions 82 relative to each other in two directions.

Each seal portion 82 further includes a surface 96 defining a portion of the aperture 84 that is formed when two seal portions are joined to form a sealing block 80. Similarly, each seal portion 82 may further include at least one retention feature that forms a part of a retainer 86 that is formed when two seal portions are joined to form a sealing block 80.

It will be appreciated that the illustrated seal portions 82 are exemplary only and should not be considered limiting. As illustrated, the two seal portions 82 are identical to each other. In some embodiments, the seal portions are not identical. In some embodiments, the seal portions 82 include locking features 92, 94 and retention features 98 having any suitable shape, position, and number. In some embodiments, the shape of the assembled sealing block has any suitable shape to sealingly engage different recesses 62 in the associated frame 60. In some embodiments, the sealing block is a one-piece seal. In some embodiments, the sealing block is formed from three or more seal elements. These and other suitable variations to the seal portions 82 and sealing blocks 80 are contemplated and should be considered within the scope of the present disclosure. In some embodiments, the passthrough 20 includes sealing blocks 80 of different sizes, and the frame 60 is configured to accommodate differently sized sealing blocks.

As previously described with regard to FIG. 6, the illustrated seal portions 82 are assembled into a sealing block 80 that surrounds a conduit 30 and then the seal is inserted into a recess 62 in the frame 60. A similar process is conducted on the other side of the passthrough 40 so that for each conduit 30, the associated recesses 62 of both frames 60 are sealed around the conduit. For those recesses 62 that do not have a conduit 30 passing therethrough, a sealing block 80 can be inserted into the aperture after being rotated 90 degrees about a vertical axis so that the aperture 84 of the seal extends from one vertical wall 64 to the other. That is, a solid face of the sealing block 80 is exposed to the first area 22 or second area 24 so that the entire recess 62 in the frame 60 is occluded when the corresponding door 44, 46 is closed. When fully configured, each recess 62 of both frames has a sealing block 80 inserted therein so that when the first and second doors 44, 46 are closed, the only fluid connection between the first area 22 and the second area 24 is through the conduit(s) 30 extending through the passthrough.

In operation, the passthrough the door adjacent to the first space is opened and panel 48 removed. A length of conduit is placed into the passthrough, and the conduit routed through block 80 next to the first door. The first door is closed, and the door leading to the second space is opened. The coil of conduit is routed through the block 80 adjacent to the second door into the second space. Valves, fittings, connections, manifolds placed in the passthrough may be accessed by either space in turn.

FIGS. 9 and 10 show another representative embodiment of a sealing block 180 according to aspects of the present disclosure. The sealing block 180 is formed from a pair of elongate seal portions 182. Each seal portion 182 has a generally rectangular body 190 with a plurality of semi-cylindrical recesses 192 formed in one of the faces. When the seal portions 182 are assembled to form a sealing block 180, each recess 192 cooperates with a corresponding recess in the other seal portion to form a cylindrical aperture 184 through the sealing block 180.

The sealing block 180 is mounted in a frame similar to the frame 60 shown in FIGS. 4 and 5 except that there are no fewer vertical walls 64 so that the sealing block 180 can be inserted from the side or from the top. With the sealing block 180 inserted in the frame, each aperture 184 can have a conduit 30 extending therethrough or can be occluded with a plug 194. Similar to the previous embodiment, when the first and second doors 44, 46 are closed, the only fluid connection between the first area 22 and the second area 24 is through the conduit(s) 30 extending through the passthrough.

As best shown in FIG. 10, each plug 194 has a cylindrical central portion 196 with a diameter corresponding to the diameter of the cylindrical aperture 184. An end portion 198 is disposed at each end of the central portion 196. In the illustrated embodiment, each end portion 198 is a cylinder coaxial with the central portion 196 and having a larger diameter than the central portion. The end portions 198 engage the sides of the sealing block 180 to limit movement of the plug 194 in the axial direction and to further occlude the aperture 184 in the sealing block 180.

In some embodiments, two or more seals are inserted into the frame end to end. In some embodiments, the size, number, shape and location of the apertures vary to define any suitable configuration. In some embodiments, the plugs have any suitable configuration suitable for occluding the apertures in the seal. These and other variations are contemplated and should be considered within the scope of the present disclosure.

Figure 11:
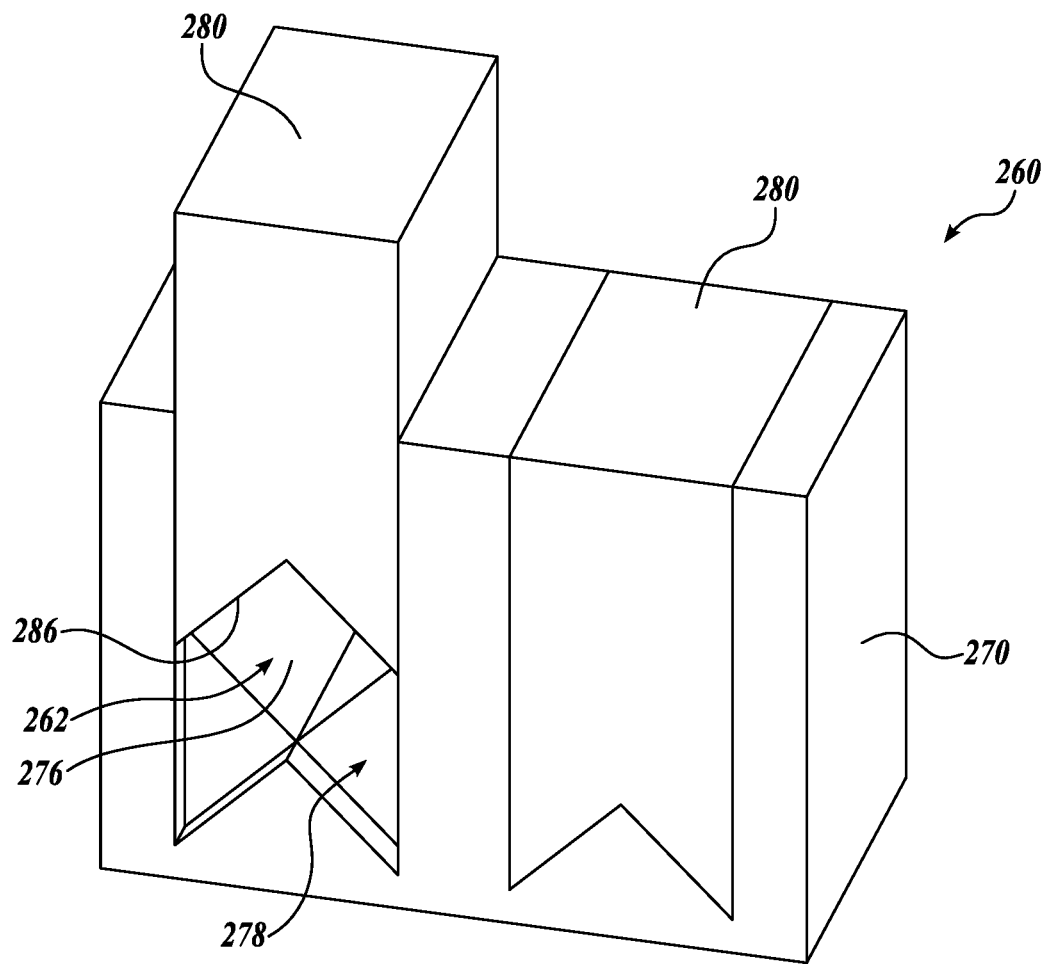
FIG. 11 an isometric view of a third representative embodiment of a sealing block suitable for use with the passthrough of FIG. 1.
Figure 12:
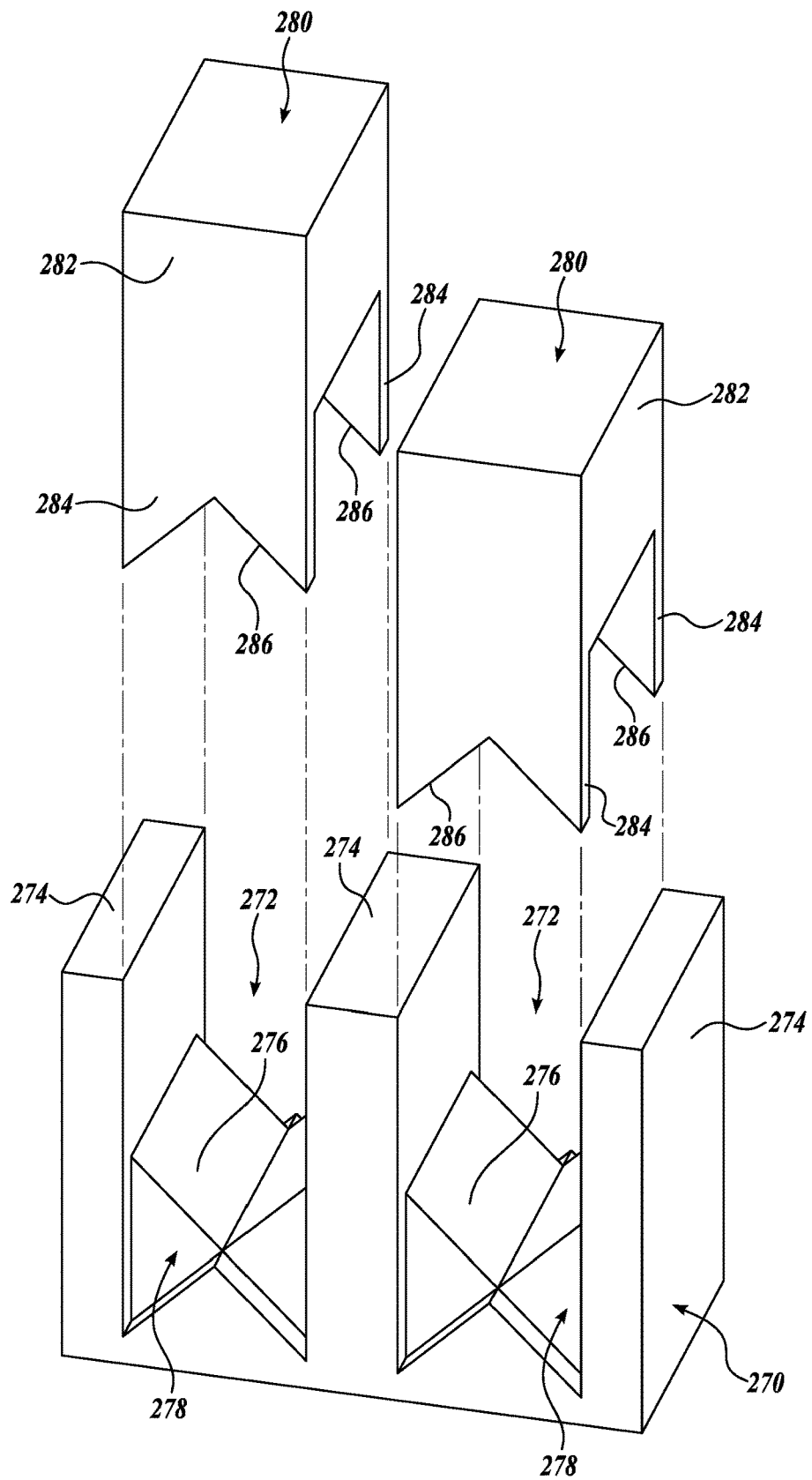
FIG. 12 shows an isometric exploded view thereof.

Referring now to FIGS. 11 and 12, another embodiment of a sealing block 260 suitable for use with the disclosed passthrough is shown. The sealing block 260 includes a rectangular base 270 and one or more plugs 280 that are selectively positionable relative to the base. The base 270 includes one or more slots 272, wherein each slot is partially defined by a pair of adjacent vertical walls 274. A base aperture surface 276 is formed at the bottom of each slot 272. In the illustrated embodiment, the base aperture surface has the profile of an upward facing "V," however, it will be appreciated that the base aperture surface may have other profiles, including a partial cylinder or any other suitable profile. A recess 278 is formed blow each slot 272, and more specifically, below the aperture surface 276 of each slot.

Each plug 280 includes a main body 282 sized and configured to be received by a slot 272 in the base 270. In some embodiments, the slots 272 and plugs 280 are sized so that a plug can be received by any of the slots. In some embodiments, there are two or more differently sized slots, each slot corresponding to a plug sized to be received by that slot.

A pair of legs 284 extend downward from the body 282 of each plug 280, and a plug aperture surface 286 is formed at the bottom of each leg 284. In the illustrated embodiment, the plug aperture surface has the profile of a downward facing "V," however, it will be appreciated that the aperture surface may have other profiles, including a partial cylinder or any other suitable profile.

As best shown in FIG. 11, the plug 280 can be fully inserted into the slot 272 to occlude the slot. With the plug 280 fully inserted, the legs 284 of the plug are engaged with the recess 278 in the base 270, and the aperture 262 is blocked. When the plug 280 is only partially inserted in the slot 272, the base aperture surface 276 and the plug aperture surface 286 define the ends of the aperture 262. In some embodiments, the conduit 30 is a flexible tube that deforms when the plug 280 is moved into the slot 272 so that the eternal surface of the conduit sealingly engages the aperture 262. In some embodiments, the base 270 and the plug 280 are deformable so that the base and plug deform to sealingly engage the external surface of conduit extending therethrough. In some embodiments, the position of the plug 280 relative to the recess 278 is maintained by an interference fit, a strap, a fastener, or any suitable means.

Figure 13:
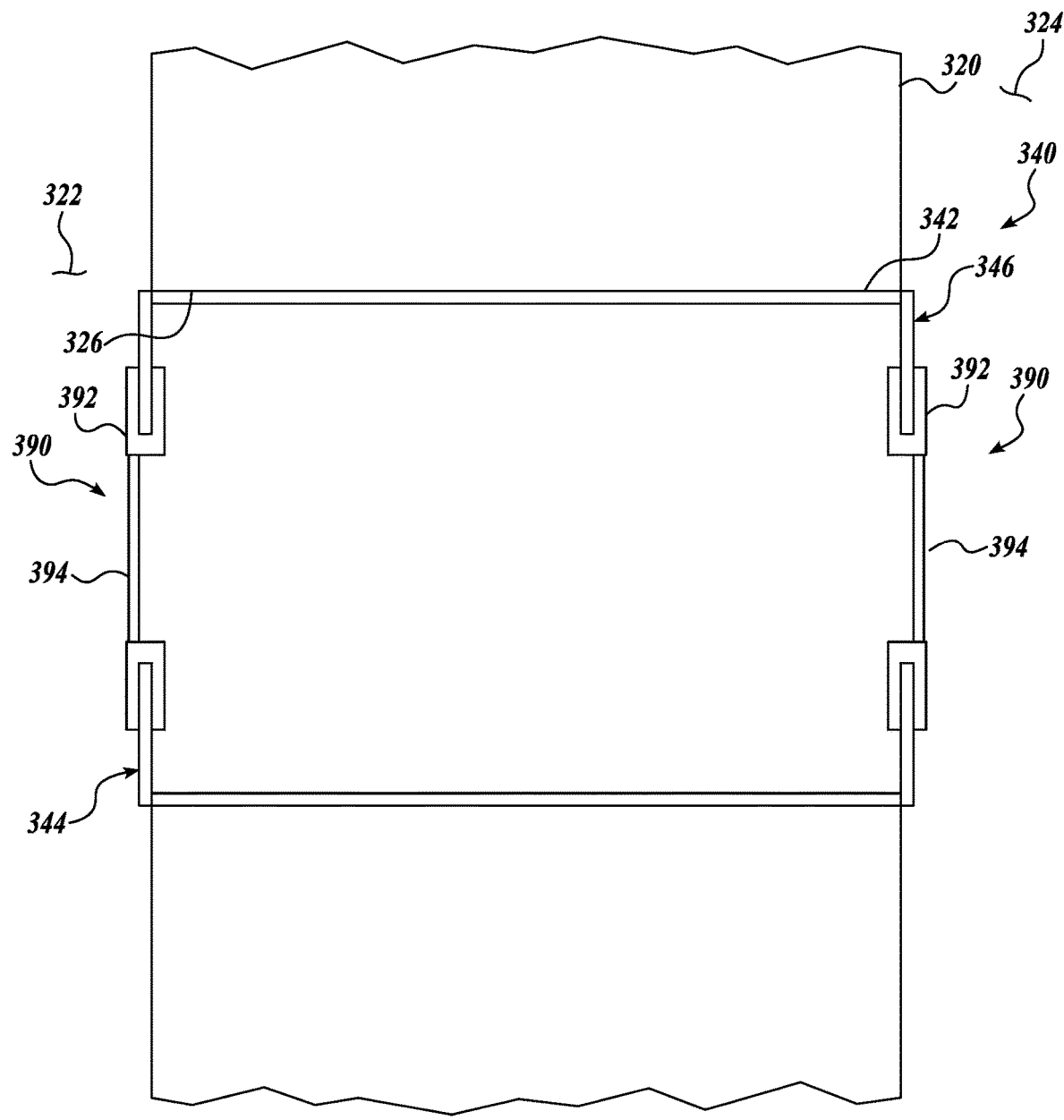
FIG. 13 shows a cross-sectional view of a fourth representative embodiment of a passthrough according to aspects of the present disclosure, wherein the passthrough is mounted in a wall.
Figure 14:
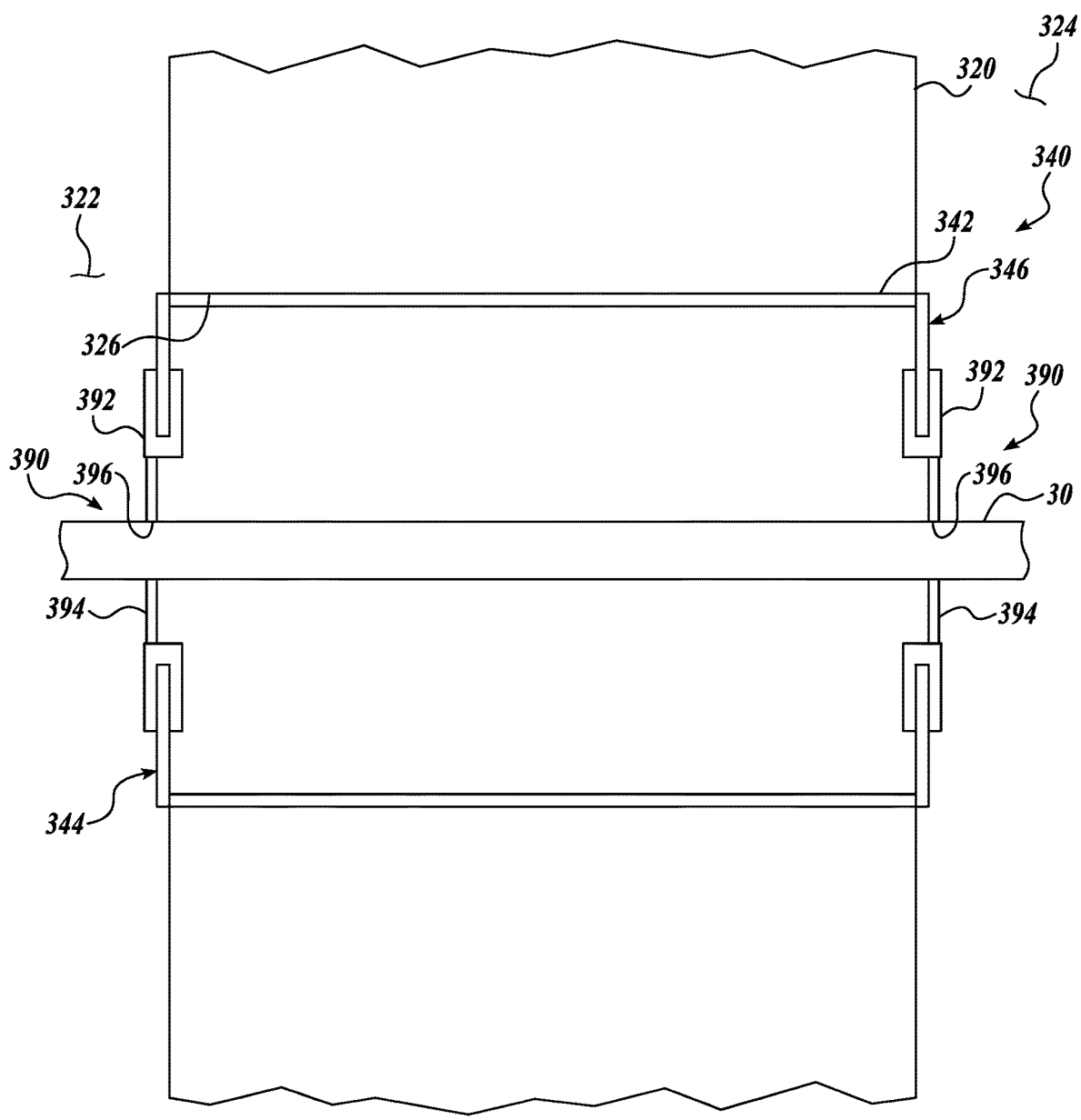
FIG. 14 shows a cross-sectional view thereof with a conduit extending through the passthrough.

FIGS. 13 and 14 show another representative embodiment of a passthrough 340 mounted to a barrier 320 that separates a first area 322 from a second area 324. Similar to the previously describe passthroughs, the illustrated passthrough 340 includes a housing 342 mounted to an aperture 326 that extends through the barrier 320. First and second doors 344 and 346 are hingedly coupled to opposite ends of the housing 342. Each door is selectively moveable between (1) a closed position, in which the door isolates the interior of the passthrough 340 from the adjacent area 322 and 324, respectively, and (2) an open position, in which a user can access the interior of the passthrough from the corresponding area.

A diaphragm valve 390, such as an iris valve, is mounted to each door 344 and 346. Each valve 390 includes a base 392 mounted to an aperture in the door and a diaphragm 394 mounted to the base. In a first state, shown in FIG. 13, the diaphragm 394 cooperates with the base 392 so that the valve 390 and the door 344, 346 to which the valve is mounted isolate the interior of the housing 342 from the adjacent area 322, 324. As shown in FIG. 14, the valve 390 is selectively moveable to a second position in which the diaphragm defines an aperture 396 extending therethrough. The aperture 396 is configured to sealingly engage the outer surface of a conduit 30 that passes through the valve 390.

In some embodiments, the aperture is configured to provide an aperture having a variable diameter in order to accommodate different sized conduits. In some embodiments, the valve is opened so that the conduit slides relative to the valve when the door is opened. In some embodiments, the conduit is flexible, and an excess length of the conduit is disposed within the passthrough so that the door can be opened without opening the valve, i.e., the portion of the conduit engaging the valve moves with the door when the door is opened, and the excess conduit within the passthrough extends to accommodate the opening of the door. These and other variations in the cooperation of the valve with the conduit are contemplated and should be considered within the scope of the present disclosure.

Figure 15:
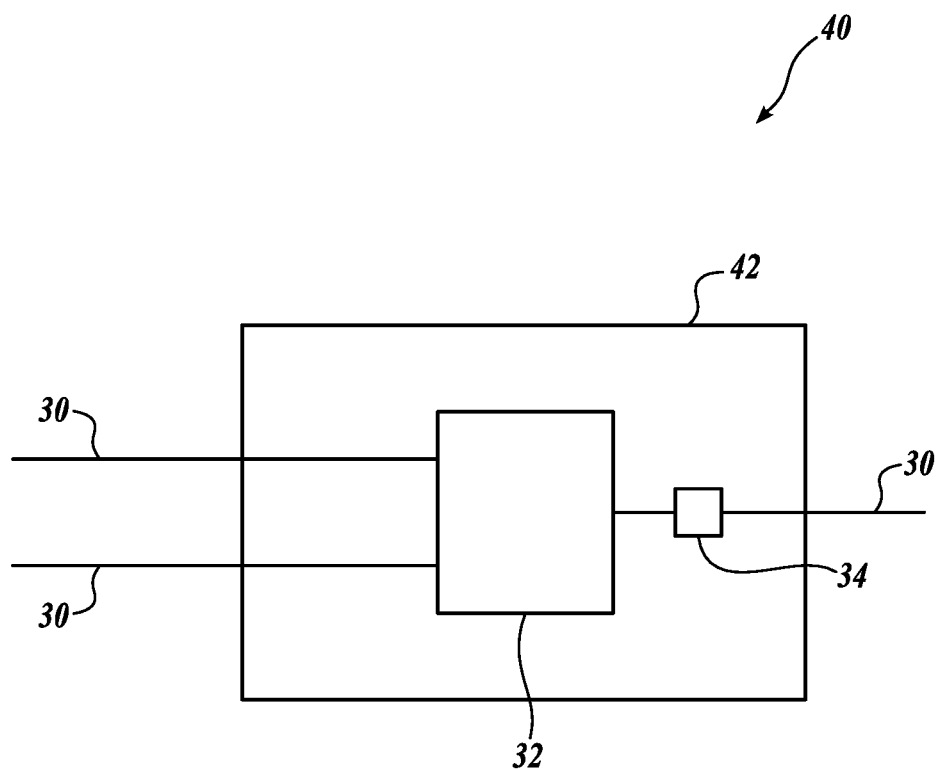
FIG. 15 shows a schematic view of the passthrough of FIG. 1 with a manifold and a valve disposed within a housing of the passthrough.

In some embodiments, a manifold is disposed within the passthrough to provide a fluid connection between different numbers of conduits on each side of the passthrough, e.g., a single conduit on one side of the passthrough is in fluid connection with two or more conduits on the other side of the passthrough. In some embodiments, one or more valves are disposed within the passthrough to selectively block the transfer of fluid through the passthrough. FIG. 15 shows a non-limiting embodiment of the passthrough 40 of FIG. 1 with a manifold 32 and a valve 34 positioned within the housing 42. In some embodiments, the passthrough is accessible from three or more rooms, such as when the passthrough is located in a corner and includes walls in multiple adjacent rooms.

In some embodiments, the frame is coupled to one or both doors of the passthrough. In some embodiments, the frame is fixedly coupled to the barrier, separate from the housing.

The principles, representative embodiments, and modes of operation of the present disclosure have been described in the foregoing description. However, aspects of the present disclosure, which are intended to be protected, are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure as claimed.

The embodiments of the invention in which an exclusive property or privilege is claimed are defined as follows:

1. A passthrough, comprising:
    a barrier separating a first space from a second space, the barrier having a first side at least partially defining a portion of the first space and a second side at least partially defining a portion of the second space, the barrier further including an opening extending from the first space to the second space;
    a housing mounted to the barrier and extending through the opening, the housing defining a passageway extending from the first side of the barrier to the second side of the barrier, the housing including a first door selectively separating at least a portion of the opening from the first space and a second door selectively separating at least a portion of the opening from the second space;
    a first sealing block having a first aperture extending therethrough in a first axial direction;
    a second sealing block having a second aperture extending therethrough in a second axial direction;
    a first frame disposed within the housing and having a first recess proximate to the first space, the first recess being partially defined by a first inner wall and being sized and configured to slidably receive the first sealing block from the first space, movement of the first sealing block toward the second side of the barrier being limited by the first inner wall; and
    a second frame disposed within the housing and having a second recess proximate to the second space, the second recess being partially defined by a second inner wall and being sized and configured to slidably receive the second sealing block from the second space, movement of the second sealing block toward the first side of the barrier being limited by the second inner wall,
    wherein the passthrough is configured to have a first state and a second state such that:
    in the first state, the first and second sealing blocks are oriented within the first and second recesses, respectively, so that at least one end of the first aperture is occluded by the first frame, and at least one end of the second aperture is occluded by the second frame, and
    in the second state, the first and second sealing blocks are oriented within the first and second recesses, respectively, so that the first aperture extends from the first space toward the second space, and the second aperture extends from the second space toward the first space.

2. The passthrough of claim 1, further comprising a first conduit extending through the first aperture and the second aperture when the passthrough is in the second state, the first conduit sealingly engaging the first and second apertures.

3. The passthrough of claim 2, further comprising a valve disposed within the housing, wherein the valve selectively controls a flow of fluid through the first conduit.

4. The passthrough of claim 2, further comprising:
    a second conduit extending into the housing; and
    a manifold disposed within the housing and fluidly connecting the first and second conduits.

5. The passthrough of claim 1, wherein the first and second doors and the first and second sealing blocks cooperate to isolate the first space from the second space when the passthrough is in the first state.

6. The passthrough of claim 1, wherein the first and second doors cooperate with the first and second sealing blocks, respectively, and the first and second frames, respectively, to isolate the passageway from the first and second spaces when the passthrough is in the second state and each of the first and second doors is in a closed position.

7. The passthrough of claim 1, wherein the first aperture is fluidly isolated from the first space when the passthrough is in the first state.

8. The passthrough of claim 7, wherein the second aperture is fluidly isolated from the second space when the passthrough is in the first state.

9. The passthrough of claim 1, wherein the first and second frames are integrally formed with each other.

10. The passthrough of claim 1, wherein the first sealing block engages the first frame and the first door to block fluid communication between the passageway and the first space when the passthrough is in the first state and the first door is in a closed position.

11. The passthrough of claim 1, wherein the first sealing block comprises a first portion engaging a second portion to define the first aperture.

12. The passthrough of claim 11, wherein the first portion is identical to the second portion.

13. The passthrough of claim 1, further comprising a plug sized and configured to be inserted into the aperture of the first sealing block, wherein the plug occludes the aperture of the first sealing block when inserted in the aperture.

14. The passthrough of claim 1, further comprising a panel supported by the first and second frames and dividing the passageway into first and second portions.

15. The passthrough of claim 1, wherein the first door cooperates with the first sealing block and the first frame to isolate the first space from the second space when the passthrough is in the first state and the first door is in a closed position.

16. The passthrough of claim 1, wherein the first door cooperates with the first sealing block and the first frame to isolate the first space from the passageway when the passthrough is in the first state and the first door is in a closed position.

17. The passthrough of claim 15, wherein the second door cooperates with the second sealing block and the second frame to isolate the second space from the passageway when the passthrough is in the first state and the second door is in a closed position.

* * * * *